United States Patent [19]

Lin et al.

[11] Patent Number: 5,587,512
[45] Date of Patent: *Dec. 24, 1996

[54] PROCESS FOR OBTAINING [S,S]-ETHYLENEDIAMINE-N,N'-DISUCCINIC ACID FROM A SALT SOLUTION OF SUCH ACID AND L-ASPARTIC ACID

[75] Inventors: Ronny W. Lin, Baton Rouge; Eldon E. Atkinson, Jr., Greenwell Springs; Donald E. Balhoff, Baton Rouge, all of La.

[73] Assignee: Albemarle Corporation, Richmond, Va.

[ * ] Notice: The term of this patent shall not extend beyond the expiration date of Pat. No. 5,466,867.

[21] Appl. No.: 272,457

[22] Filed: Jul. 11, 1994

[51] Int. Cl.$^6$ ................................................ C07C 229/00
[52] U.S. Cl. ............................................................ 562/565
[58] Field of Search ............................................... 562/565

[56] References Cited

U.S. PATENT DOCUMENTS

| | | | |
|---|---|---|---|
| 3,158,635 | 11/1964 | Kezerian et al. | 260/429 |
| 4,704,233 | 11/1987 | Hartman et al. | 252/527 |
| 5,466,867 | 11/1995 | Lin | 562/554 |

FOREIGN PATENT DOCUMENTS 558905  8/1977  U.S.S.R. .

OTHER PUBLICATIONS

Neal, et al., "Stereospecific Ligands and Their Complexes, I. A. Cobalt(III) Complex of Ethylenediaminedisuccinic Acid[1]", *Journal of Inorganic Chemistry*, vol. 7, No. 11, Nov. 1958, pp. 2405–2412.

*Primary Examiner*—Michael L. Shippen
*Attorney, Agent, or Firm*—E. E. Spielman, Jr.

[57] ABSTRACT

This invention relates to a method for obtaining [S,S] ethylenediamine-N,N'-disuccinic acid precipitate from an aqueous solution of the salts of such acid and L-aspartic acid.

12 Claims, No Drawings

PROCESS FOR OBTAINING [S,S]-ETHYLENEDIAMINE-N,N'-DISUCCINIC ACID FROM A SALT SOLUTION OF SUCH ACID AND L-ASPARTIC ACID

BACKGROUND OF THE INVENTION

This invention relates to an effective and facile method for obtaining [S,S]-ethylenediamine-N,N'-disuccinic acid from an aqueous solution of the salts of such acid and L-aspartic acid.

Ethylenediamine-N,N'-disuccinic acid (EDDS) and its various alkali metal, alkaline earth metal, ammonium and substituted ammonium salts are well recognized by the detergent industry as useful chelating agents in cleaning formulations. (See U.S. Pat. No. 4,704,233, which is incorporated herein by reference as if fully set forth.) These salts and acids are theorized to chelate metals such as iron, manganese, copper and other multivalent metal ions. The metal ions are constituents of certain organic stains or act to stabilize such stains when present in washing solutions. Besides providing for the chelating function, EDDS and its salts are non-phosphorous compounds and, as a result, are environmentally desirable. Even further, EDDS and its salts exhibit biodegradability. The degree of biodegradability depends upon the optical EDDS isomer involved. Of the three optical isomers, [R,R], [R,S] and [S,S], the [S,S] isomer is most easily biodegradable and is thus preferred.

The [S,S] isomer can be synthesized from L-aspartic acid and 1,2-dibromoethane. A particularly attractive route features reacting the aspartic acid as sodium L-aspartate with 1,2-dibromoethane in a basic aqueous medium to yield, in solution, the sodium salts of [S,S] EDDS. See Neal and Rose, *Stereospecific Ligands and Their Complexes of Ethylenediamine-disuccinic Acid, Inorganic Chemistry*, Vol. 7. (1968), pp. 2405–2412. The Neal and Rose process reacts most of the L-aspartic, with typically less than 60% of the reacted L-aspartic acid being converted to the sodium salt of [S,S] EDDS. The remainder is converted to by-products, such as, oligomers, 2-hydroxyethylamine N-succinic acid and 2-bromoethylamine N-succinic acid, and other heavies.

According to Neal and Rose, the EDDS can be recovered from the solution by slowly acidifying the solution with concentrated hydrochloric acid to obtain a pH of 3.5. The acidification converts the [S,S] EDDS salt to the acid, which acid crystallizes and precipitates from the solution. Fine crystals are said to precipitate out as the pH moves between pH 7 and 3.5. To purify the EDDS precipitate, the precipitate is recovered and redissolved in a NaOH solution followed by reacidification. The cycle is repeated two times. The final precipitate is washed with water to remove HCl and any traces of L-aspartic acid. This procedure is burdened with poor L-aspartic acid utilization, lengthy process time, and high HCl consumption in the purification cycles.

The L-aspartic acid utilization can be substantially improved if, instead of reacting almost all of the L-aspartic acid (as the salt) per Neal and Rose, a smaller portion is reacted, say less than about 60 mole %. In this way, it has been found that most of the L-aspartic acid reacted is converted to [S,S] EDDS (as the salt) and that very little of the reacted L-aspartic acid goes to the production of by-products. However, the low amount of L-aspartic acid reacted presents a significant problem to the facile recovery of [S,S] EDDS. The problem resides in the fact that the substantial amount of unreacted L-aspartic acid salt in the reaction solution will co-precipitate out with the [S,S] EDDS precipitate when the solution is acidified as per Neal and Rose. Due to the large amount of the L-aspartic acid precipitate, the resultant product is not of acceptable purity.

It is, therefore, an object of this invention to provide a simple and efficient method for recovering relatively pure [S,S] EDDS from an aqueous solution containing L-aspartic acid salt and EDDS acid salt.

The Invention

This invention features a method for obtaining a high yield of relatively pure [S,S] EDDS from solutions containing [S,S] EDDS salt and L-aspartic acid salt. With this method, co-precipitation of L-aspartic acid is greatly reduced.

More particularly, the method of this invention obtains [S,S] EDDS from an aqueous solution containing [S,S] EDDS salt and L-aspartic acid salt by co-feeding, to a volume of water, (1) the aqueous solution and (2) an aqueous mineral acid having a dissociation constant within the range of from about $1.0 \times 10^{-1}$ to about $1.0 \times 10^{10}$, wherein the feed rates of the aqueous solution and the aqueous mineral acid are controlled so that the volume of water has a pH within the range of from about 2 to about 6.5 at least substantially throughout the co-feed period. It is preferred that the pH be within the range of from about 2.4 to about 5.5 and most highly preferred that the pH lie within the range of from about 2.6 to about 5.

The L-aspartic acid salt solute and the [S,S] EDDS salt solute in the aqueous solution will generally be alkali metal salts, alkaline earth metal salts, ammonium salts, substituted ammonium salts or a mixture of two or more of the foregoing. Preferred salts are the alkali metal salts with the sodium and potassium salts being more preferred. The most preferred salt is the sodium salt.

The aqueous solution can have a wide range of salt concentrations. The method of this invention is particularly useful in those cases where the L-aspartic acid salt comprises at least 2 wt % of the solution while the [S,S] EDDS salt comprises at least 1 wt % of the solution. It is anticipated that the method of this invention will be practiced most with aqueous solutions having an L-aspartic acid salt concentration within the range of from about 4 to about 50 wt % of the solution and a [S,S] EDDS acid salt concentration within the range of from about 2 to about 50 wt % of the solution. When the aqueous solution is derived from a [S,S] EDDS process in which there is low conversion of the L-aspartic acid, the solution can have a L-aspartic acid salt concentration within the range of from about 4 to about 40 wt % of the solution and a [S,S] EDDS acid salt concentration within the range of from about 2 to about 30 wt % of the solution.

Prior to its being co-fed to the volume of water, the aqueous solution will be basic. Generally, the aqueous solution will have a pH which is within the range of from about 8 to about 13, and usually within the range of from about 8.5 to about 12. When the solution salts are principally sodium salt, then the solution pH is usually within the range of from about 8.5 to about 11.5.

The aqueous solution can be from any source, its origin is not critical. The solution can contain other constituents, e.g., soluble salts other than those mentioned herein, provided that the constituent does not frustrate the operation of the method of this invention.

Suitable mineral acids are those having a dissociation constant within the range of from about $1.0 \times 10^{-5}$ to about $1.0 \times 10^{10}$. Exemplary of such acids are hydrohaloic acids, sulfuric acid, phosphoric acid and mixtures of any two or more of the foregoing. Hydrohaloic acids and sulfuric acid are preferred, with hydrochloric acid being most preferred. Preferred aqueous hydrochloric acid solutions are the concentrated solutions and more preferred are those which contain 2 to 40 wt % HCl. Most highly preferred are those containing from about 5 to about 37 wt % HCl.

The volume of water to which the aqueous solution and the aqueous mineral acid solution are co-fed serves many purposes. It acts as a mixing medium to effect the efficient mixing of the two co-fed solutions. Also, the volume of water acts as a crystallization medium which dilutes the two solutions as they are co-fed so that controlled precipitation is effected. Without dilution, supersaturation is possible. The volume of water also provides sufficient volume to dissipate the heat of neutralization. Even further, the volume of water provides sufficient water to hold the by-product salts of neutralization, e.g., NaCl, in solution so that they will not precipitate out. Finally, the volume of water provides for a sufficient volume so that the pH of the system can be conveniently measured, especially at the beginning of the co-feed. The size of the volume of water will increase over time as the two co-fed solutions bring water to the reaction system. Thus, with the volume of water ever increasing in size, the initial size of the volume of water is the main concern. The determination of a suitable initial water volume is best determined empirically with the goal being the accomplishment of the above recited functions. The empirical determination should consider the pH of the solutions co-fed, the salt or acid concentrations of the solutions co-fed, the volume feed rate of the co-fed solutions, and the precipitate quality desired. Generally speaking, the initial volume of water will provide a ratio of the water volume initially present before co-feed to the total volume of the solutions to be co-fed which lies within the range of from about 1:0.1 to about 1:5 and most preferably within the range of from about 1:0.2 to about 1:2.5. The size of the volume of water at any point during the co-feed period will be determined by the sum of the initial size of the volume of water and the amount of water introduced by the co-feed solutions, minus any water losses from the reaction system.

It is to be understood that the volume of water will contain various solutes, e.g., L-aspartate, inorganic salts and small amount of [S,S] EDDS. The identities and the concentrations of the solutes will most likely change during the co-feed period. The [S,S] EDDS concentration will not increase dramatically as most all of it will be precipitating out of the solution as the acid during the co-feed period.

It is preferred that the volume of water have an essentially neutral or preacidified pH, i.e., one within the range of from about 2 to about 8 before the co-feed begins.

By the term "co-feed", it is meant that the feeds of the aqueous solution and the aqueous mineral acid occur together timewise or in alternating portions. When fed together, it is not a deviation from the method of this invention to start or finish one feed slightly before or after the other, or to have one feed interrupted for a short period of time, provided that the pH of the volume of water stays within the prescribed range for the prescribed period of time. The rate of feed for each feed is adjusted in response to maintaining the pH of the volume of water at the desired level. If the water volume becomes too basic, then the mineral acid solution feed rate is increased or the aqueous solution feed rate is decreased. The reverse is true if the volume of water becomes too acidic.

The alternating feed technique for effecting the co-feed features the intermittent addition of a portion of one of the feeds and then a portion of the other feed, with attention given to obtaining and maintaining the prescribed acidic pH substantially throughout the precipitation period. For example, a portion of the aqueous mineral acid is added until the prescribed water volume pH is obtained. Then a portion of the aqueous solution is added with care being taken to not leave the pH range. Another portion of the aqueous mineral acid is then added followed by another portion of the aqueous solution. The sequence is repeated until all of the acid and salt have been added.

The pH adjustments are made by measuring the pH of the water volume and, for these measurements, determining what adjustment, if any, is needed to obtain the desired pH. The pH values recited for the methods of this invention are obtained by the use of conventional pH meters with their probes located in the water volume.

The method of this invention best occurs at any temperature at which the solutions and volume of water do not boil or freeze. It is preferred that the pressure be around ambient pressure. The temperature is preferably within the range of from about 5° to about 55° C.

After the co-feed is finished, a wet cake is formed by the recovery of precipitates from the volume of water. The recovery can be by filtration or centrifugation. After the recovery, the wet cake, which is essentially all [S,S] EDDS, is preferably washed with water to reduce the impurities content.

In its broadest definition, the method of this invention accomplishes the selective precipitation of [S,S] EDDS over L-aspartic acid from an aqueous solution of the salts of these two acids by exposing the salts to a pH which is favorable to the precipitation of [S,S] EDDS over the precipitation of L-aspartic acid throughout substantially all of the period during which precipitation of either of the acids occur. It is stated "throughout substantially all of the period" because there may be an initial adjustment period in which the pH may stray, but that period is short and is measured in seconds to minutes, say 5 seconds to 10 minutes.

The following Examples are meant to illustrate the methods of this invention and are not to be taken as limiting the scope thereof.

EXAMPLE I

Comparative Example

To a 500 cc flask, 120.8 g of a SS EDDS reaction solution were charged, which had 13.43 wt % L-aspartic acid and 7.81 wt % SS EDDS (as their sodium salts). 24.4 g of 36.5 wt % hydrochloric acid were added to the solution for about 15 minutes to bring the pH from 10.5 (at 25° C.) to 3 (at 38° C.) to obtain a slurry. The slurry was cooled down to 30° C. (while the pH was slightly increasing) and then vacuum-filtered. The filtrate (75 g) had a pH of 4 and contained 3.63 wt % L-aspartic acid and 5.70 wt % SS EDDS. Washing the cake with water on the filter gave 80.1 g wash solution (pH =4.5) having 1.40 wt % L-aspartic acid and 1.37 wt % EDDS. The washed wet cake had 32.58 wt % L-aspartic and 10.72 wt % SS EDDS.

EXAMPLE II

Comparative Example 21 g of 36.5 wt % HCl solution were charged into a 500 cc flask. A SS EDDS reaction solution (13.33 wt % L-aspartic acid and 8.26 wt % SS EDDS) were added slowly.

During the addition a slurry was formed which subsequently dissolved. When 106 g of the reaction solution was added at 20°–37° C. for 20 minutes, a clear solution was obtained with a pH of 3, which precipitated quickly. Additional 39 g of the reaction solution were added. The slurry was filtered and the resultant wet cake was washed with water. 141 g of total filtrate (pH=4.5) had 5.42 wt % L-aspartic acid and 6.34 wt % SS EDDS. The wet cake (46.2 g) had 24.62 wt % L-aspartic acid and 8.62 wt % SS EDDS.

The following Examples are of this invention.

EXAMPLE III 7 g of 18.5 wt % hydrochloric acid and 20 g of a basic solution (containing 11.83 wt % L-aspartic acid and 10.04 wt % SS EDDS were co-fed to 37.2 g of water at ambient temperature. The pH was maintained at about 2.3–2.4 during the co-feed. The resultant slurry was immediately filtered and the cake was washed with ~35 g of water. 2.2 g of wet cake had 1.23 wt % L-aspartic acid and 43.19 wt % SS EDDS while the filtrate or mother liquor (50.2 g) had 3.45 wt % L-aspartic acid and 0.25 wt % SS EDDS.

EXAMPLE IV 225 g of water were added to 199 g of dried and 24 g of wet SS EDDS/L-aspartic acid solid, total containing 46.04 g of L-aspartic acid and 156.29 g of SS EDDS. 168 g of 40 wt % NaOH were slowly added to the mixture to dissolve SS EDDS/L-aspartic acid with an ice/water bath for cooling. 610 g of the solution were co-fed with 293.3 g of 18.5 wt % HCl solution into 1517 g of a water wash (having ~0.51 wt % L-aspartic acid and ~0.10 wt % SS EDDS) at a pH of 3.94–4.00 at 22°–26° C. for 1.7 hours. After 0.3-hour stirring, the slurry was vacuum-filtered and washed with 500 g of water. 2651 g of filtrate had 2.05 wt % l-aspartic acid and 0.22 wt % SS EDDS. 263 g of the filter cake had 0.23 wt % L-aspartic acid and 65.42 wt % SS EDDS.

What is claimed:

1. A method for obtaining [S,S] ethylenediamine-N,N'-disuccinic acid from an aqueous solution containing [S,S] ethylenediamine-N,N'-disuccinic acid salt and L-aspartic acid salt by co-feeding, to a volume of water, (1) the aqueous solution and (2) an aqueous mineral acid having a dissociation constant within the range of from about $1.0 \times 10^{-5}$ to about $1.0 \times 10^{10}$, wherein the feed rates of the aqueous solution and the aqueous mineral acid are controlled so that the volume of water has a pH within the range of from about 2 to about 6.5 at least substantially throughout the co-feed period.

2. The method of claim 1 wherein the L-aspartic acid salt and the [S,S] ethylenediamine-N,N'-disuccinic salt in the aqueous solution are the alkali metal salts, alkaline earth metal salts, ammonium salts, substituted ammonium salts or a mixture of two or more of the foregoing.

3. The method of claim 2 wherein the L-aspartic acid salt and the [S,S] ethylenediamine-N,N'-disuccinic salt are the alkali metal salts.

4. The method of claim 3 where the L-aspartic acid salt and the [S,S] ethylenediamine-N,N'-disuccinic salt are the potassium salts, the sodium salts or a mixture thereof.

5. The method of claim 1 wherein the L-aspartic acid salt comprises at least 2 wt % of the aqueous solution and the [S,S] ethylenediamine-N,N'-disuccinic acid salt comprises at least 1 wt % of the aqueous solution.

6. The method of claim 1 wherein the mineral acid is a hydrohaloic acid or a sulfuric acid.

7. The method of claim 1 wherein the aqueous mineral acid solution is a hydrochloric acid solution.

8. The method of claim 7 wherein the aqueous hydrochloric acid solution contains from about 2 to about 40 wt % HCl.

9. The method of claim 1 wherein the volume of water will provide a ratio of the water volume initially present before co-feed to the total volume of the solutions to be co-fed which lies within the range of from about 1:0.05 to about 1:5.

10. The method of claim 9 wherein the ratio is within the range of from about 1:0.1 to about 1:2.5.

11. The method of claim 1 wherein the pH is within the range of from about 2.4 to about 5.5.

12. The method of claim 1 wherein the pH is within the range of from about 2.6 to about 5.

* * * * *